United States Patent [19]

Daffer et al.

[11] Patent Number: 5,891,186
[45] Date of Patent: *Apr. 6, 1999

[54] PHYSICAL THERAPY HEATED PERSONAL CAPSULE

[75] Inventors: Steven J. Daffer, Edina; Roger E. Mitchell, Bloomington; Darren M. Laham, Burnsville, all of Minn.

[73] Assignee: Visibelle Derma Institute, Inc., Edina, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 559,036

[22] Filed: Nov. 15, 1995

[51] Int. Cl.⁶ .................................................. A61N 5/00
[52] U.S. Cl. ............................ 607/91; 607/88; 600/21; 600/27
[58] Field of Search .................... 601/23, 24, 46–56; 607/1, 2, 88, 90–95; 600/21, 27, 22

[56] References Cited

U.S. PATENT DOCUMENTS

| | | | |
|---|---|---|---|
| D. 326,720 | 6/1992 | Garrison et al. | D24/202 |
| D. 340,992 | 11/1993 | Garrison | D24/202 |
| 4,565,188 | 1/1986 | Hardie | 128/24.2 |
| 4,671,284 | 6/1987 | Wilson et al. | 128/373 |
| 4,712,538 | 12/1987 | Hardie et al. | 128/24.1 |
| 4,884,574 | 12/1989 | Hardie et al. | 128/373 |
| 5,101,809 | 4/1992 | Daffer et al. | 128/33 |

*Primary Examiner*—Robert L. Nasser
*Attorney, Agent, or Firm*—Westman, Champlin & Kelly, P.A.

[57] ABSTRACT

A personalized capsule used for physical therapy that has an elongated horizontally extending bed on a portable base, which is designed to support a person in a horizontal position. The bed is covered with an overlying cover that encapsulates the person on the bed, while leaving the head exposed, and provides selected heat, bed vibrations, lamps, and heated air to warm the entire body to desired levels for physical therapy purposes. The dry heat provided by the heating system aides in improving circulation, and also temporarily relieves aches and pains as well as relaxing muscles. The cover is provided with window openings covered by transparent windows so that the patient can be observed. The windows pivot open for manipulation or other treatment of the patient without opening the entire cover.

9 Claims, 5 Drawing Sheets

PHYSICAL THERAPY HEATED PERSONAL CAPSULE

BACKGROUND OF THE INVENTION

The present invention relates to a personalized enclosure which has a bed for supporting a patient, and a cover which encloses the body below the neck. A flow of heated air is used for raising the body temperature while the bed is vibrated selectively for temporarily providing a state of well being. The enclosure cover has large access windows for observing the patient and for access for moving or adjusting the patient for comfort and treatment.

In the prior art, it is well known to provide an individual compartment or capsule for a personalized sauna which will permit a patient to lie on a bed that can be selectively vibrated while heat is provided, and which is used for providing a feeling of well being for the person lying in the bed. Total enclosure is usually provided, as shown in U. S. Pat. No. 5,101,809. Additionally, attachments can be made for providing bright light therapy to this type of a capsule, as shown in co-pending application Ser. No. 08/340,788, filed Nov. 16, 1994. The application just mentioned uses the addition of color and other light stimuli for controllable light therapy.

SUMMARY OF THE INVENTION

The present invention relates to a personalized environmental capsule or housing for permitting controlling a heated atmosphere in the capsule for the treatment of patients that have circulatory problems, chronic pain problems and for stress management. The capsule also can be used for aiding in relieving psychiatric and psychological disorders because the heat tends to relax the muscles, calm the mind, and can reduce the need for certain medications such as anti-depressants.

The capsule includes a bed or platform for supporting a person, (a patient) and having adjustable, and selective vibration devices to selectively vibrate the bed in separate sections, namely for the bed in separate sections, the lower half of the body or the upper half, or both.

The capsule is enclosed with a cover or housing that has see-through windows on the side so that: a patient's condition can be observed without raising the cover and disturbing the temperature on the interior. Further, the windows are hinged so that they will lift up and permit access to a patient through the window openings to turn the patient, adjust the bedding, or apply individual heat pads to localized sections of the body. The use of the windows greatly enhances the ultimate use of the unit as a therapeutic device. Controls are also provided so that a program can be set out for controls, including the temperature of dry heat, for thermal therapy, the intensity of the massage vibrations for circulatory therapy, a fan flow for face air, and also stereo sound can be regulated.

Programmed and preset programs are selected by a physical therapist or the user and include various temperature setting, depending on the condition of the patient and the desired treatment.

Thermal treatment for physical therapy and medical rehabilitation is a well known first line therapy alternative. Exposing the body to a dry heat, such as with the present personalized treatment capsule, increases perspiration and is known to increase blood circulation and dilate blood vessels. This will provide relief from pain and stress, and ease and relax tired muscles and thus aid in the treatment of strains, stiffness and muscle spasms.

The heated dry air flows downward over the body from a pattern of ports on the interior of the cover creating a general "air shower", and except for the head and face which is outside the environmental capsule the heat system delivers whole body therapy.

An adjustable separate dorsal heat pad can be used on the bed, for the back and thigh heating and this heating pad can extend from the shoulders to the knees. vibration will provide temporary relief from minor aches and pains and helps to ease tired and/or strained muscles. Further, providing selected intensity ultra violet lights to the skin of a patient for relief of psoriasis or other skin problems. A transparent bed is used when all sides of the patients body are to be exposed to the UV light.

The treatment capsule is mounted on locking caster wheels for providing mobility and easy cleaning beneath the unit. The clear acrylic, see-through access windows that are built into the capsule cover, are large for easy access, and they are hinged so that they can open easily utilizing normal large size cabinet hinges that are spring loaded to maintain the windows in their open position.

The unit is ready to use, in that it is self-contained, once it is plugged in.

DETAILED DESCRIPTION OF THE PREFERRED EBODIMENTS

Figure 1:
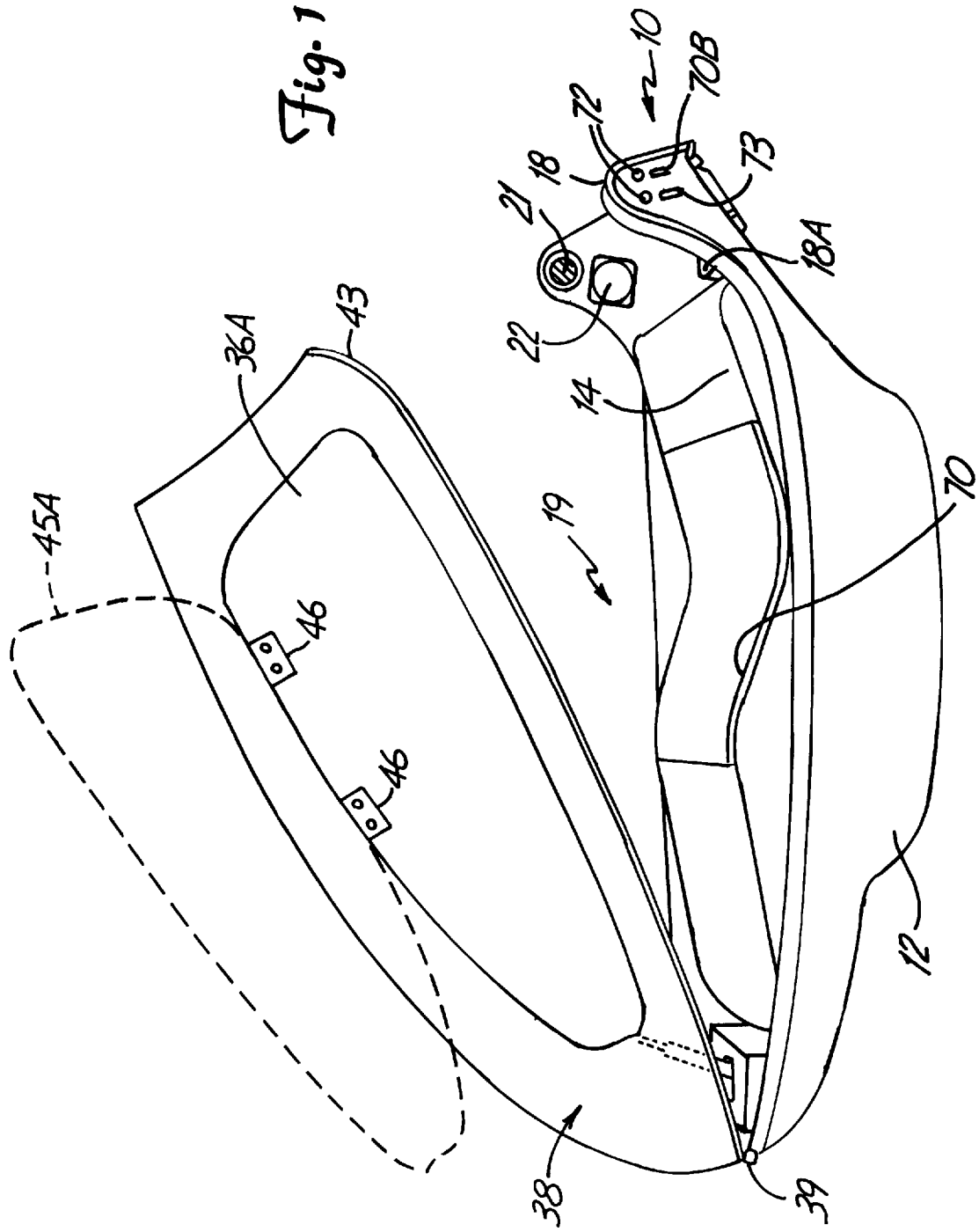
FIG. 1 is a perspective view of the physical therapy system according to the present invention.

The physical therapy heated capsule illustrated generally at 10 comprises a vibratory bed assembly 11 including a supporting pedestal 12. The interior of the pedestal provides a lower portion of a chamber or compartment 19 for a person. A blower and heated air flow duct system indicated generally at 13 (FIG. 3) provides uniformly directed, heated, recirculated air over a person in the capsule. The pedestal 12 supports a bed or cushion 14, and an individual patient shown in dotted lines in FIG. 3 at 16 is supported on the bed 14. The construction is shown essentially in U.S. Pat. No. 5,101,809. The bed 14 is mounted relative to the pedestal frame on resilient members 15, to permit vibrating the bed. The resilient members 15 are rubber balls supported in sockets 15A on the pedestal 12 and socket 15B on the supports for the bed.

As shown the capsule has a head portion 17, the pedestal including wings 18 that come up around the sides of a head of a user. A support wall 18A is used for supporting the head of the user on a suitable pillow or pad. The body compartment shown at 19 is support the entire body except for the head of the user. Wing members 18 are hollow, and provide space for air flow ducts so that cool air can be directed from an inlet, through a fan 28 and compartment 29 and through vents 21, as desired to blow across the sides of the face of the user. The fan 28 can be controlled by a suitable adjustable speed switch and the fan outlets are adjustably louvered to direct the air flow.

The pedestal 12 can be supported on suitable locking casters 25 for convenience of movement and for ease of cleaning underneath the bed assembly 14.

Suitable speakers 22 are provided for sound therapy. Stereo music or other sounds may enhance the therapeutic environment.

The blower duct system 13 provides uniformly heated, downwardly directed recirculating air. The duct system 13 is mounted on the cover member or hood 36 of the capsule, which overlies the pedestal and encloses the body compartment 19. The cover member 36 has a foot end 38 and a head end 40 which define length of the body compartment 19. The cover member 36 is hinged to the pedestal 12 at the foot end 38 and extends substantially along the entire length of the bed 14. The hinge is shown at 39 in FIG. 3.

A head end opening 42 is provided for the neck of a user so the head can extend out from the body compartment 19.

A resilient seal along the lower edges of the cover, indicated generally at 43 in FIG. 1 can be utilized for sealing the compartment 19. A main control panel 44 is provided and is accessible to an attendant and can have suitable controls as will be explained, for temperature, vibration, and sound volume, or other features used. Control switches can be on the face of the control panel of the unit or can be on a remote control panel accessible only to an attendant. For example, controls may be on the exterior of the wings 18 as will be discussed.

Figure 2:
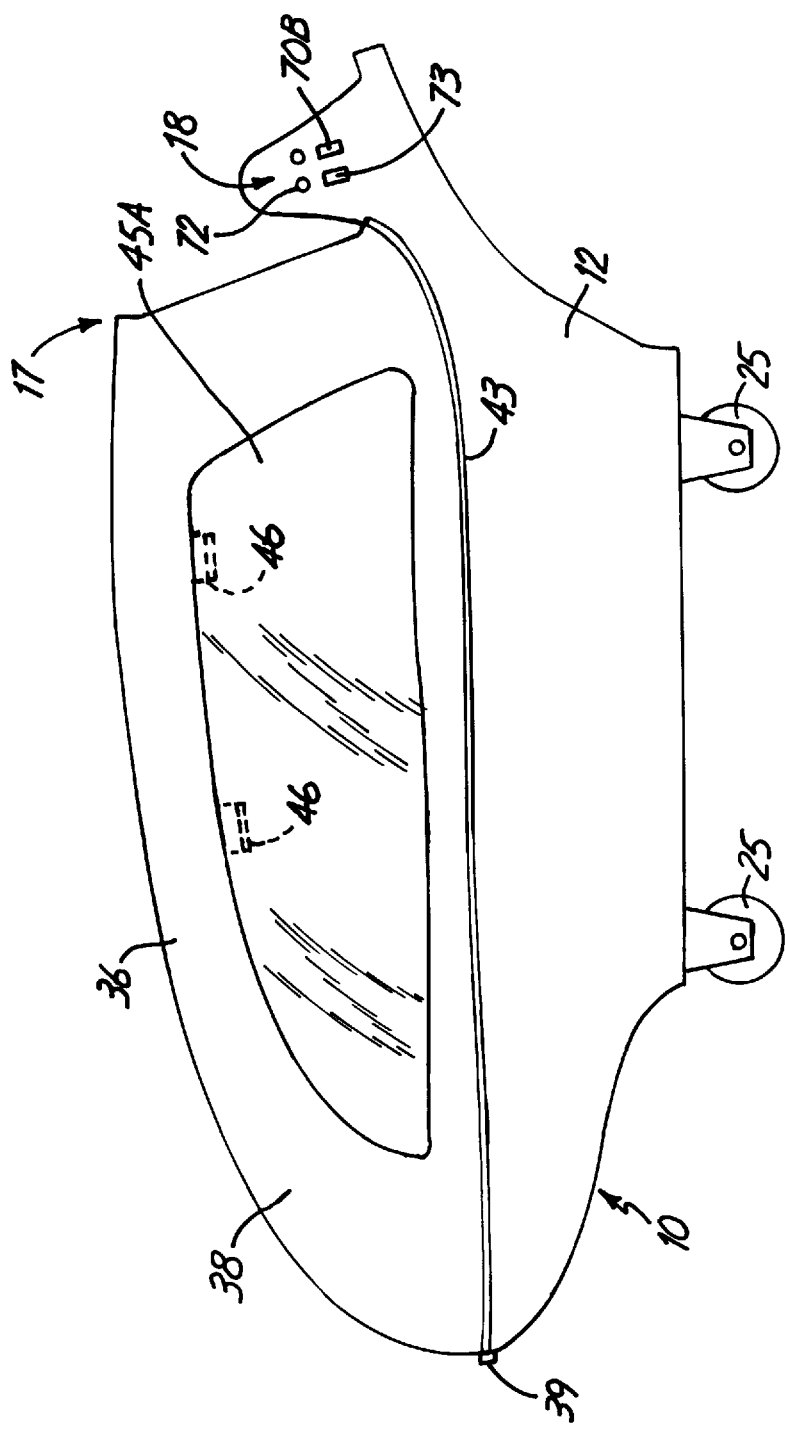
FIG. 2 is a side elevational view thereof with a housing cover in a closed position.
Figure 4:
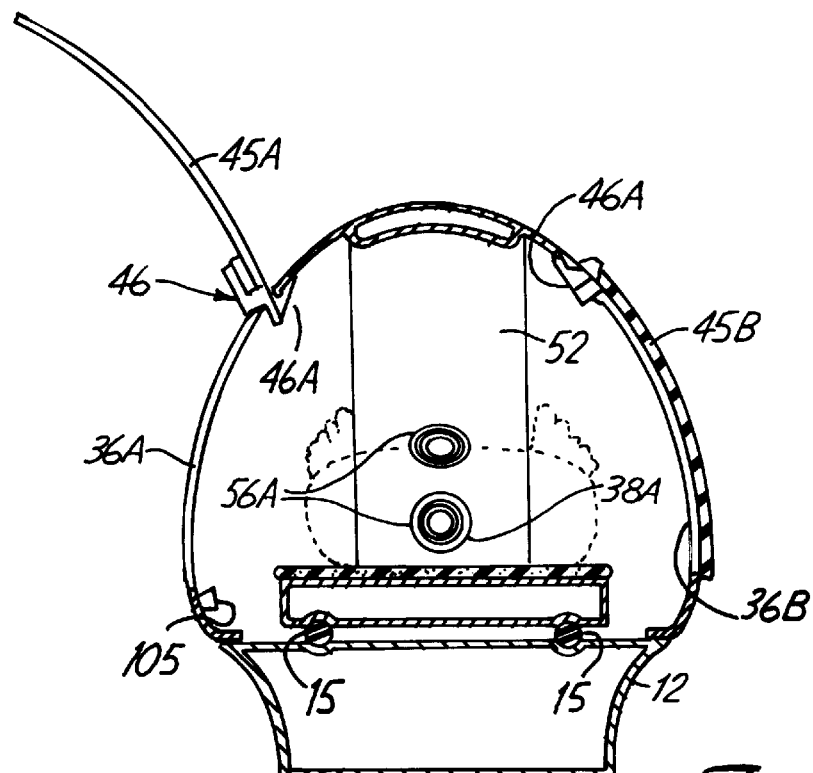
FIG. 4 is a sectional view taken along line 4—4 in FIG. 3.
Figure 5:
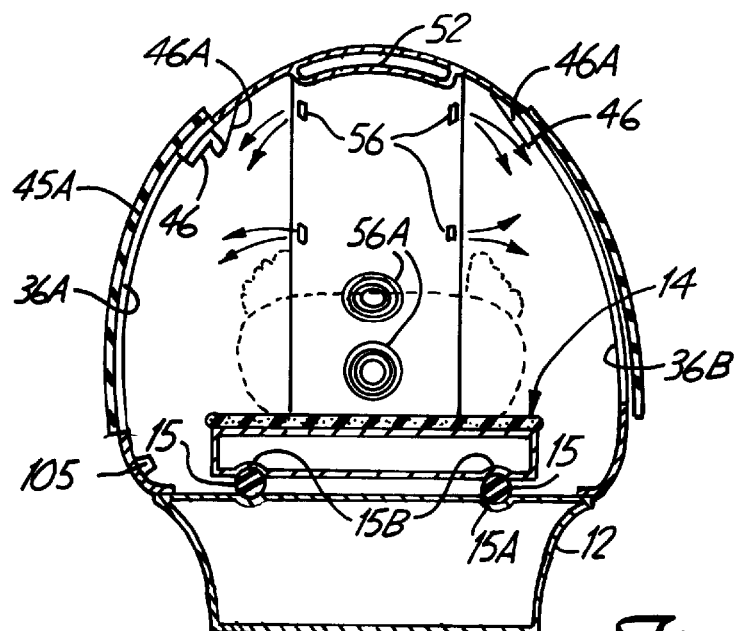
FIG. 5 is a sectional view taken along line 5—5 in FIG. 3.

The cover 36 is provided with a pair of large openings 36A and 36B, on the respective sides of the cover. The openings extend a substantial portion of the length and width of the cover, These openings are for access to a patient lying on the bed 14, and they are removably covered with clear acrylic, see-through window panels 45A and 45B, that are mounted to the main part of the cover 36 through suitable spring loaded hinges 46. The hinges can be of any desired design suitable to carry the weight of the acrylic windows 45A and 45B and are common hinges used for large cabinet doors and the like. The hinges load in the closed portion and also then spring load at the open portion. The acrylic window 45A for opening 36A is illustrated in its opened position in FIGS. 2 and 4, and the acrylic window 45A is shown in its closed position in FIGS. 4 and 5.

The hinges 46 are mounted onto suitable support blocks 46A that are molded into the top portion of the cover 36, and while shown schematically, reinforcing can be provided as desired for obtaining the necessary strength for supporting the acrylic windows and permitting them to be moved between the open and closed positions.

The acrylic windows can have suitable soft seals along their edges if desired, to seal along the peripheries of the openings 36A and 36B, respectively.

It can be seen that the large window openings 36A and 36D provide direct access to a patient lying on the bed 14, for taking care of necessary functions, such as turning, lifting, or just checking the patients condition such as taking the pulse or temperature of a patient, or performing other necessary functions.

The blower heater duct system 13 intakes air through inlets 48, and then the blower 60 will blow the air as indicated by the arrow 49 across a heater 47 and out through a blower outlet 50 and up into an interior duct 52. Outlet openings 56 are provided along sides of the duct 52 and opening 56A are provided in the center of the duct 52 to direct air as indicated by the arrows 53 downwardly over the body. This construction also is shown in U.S. Pat. No. 5,101,809. Heated (or cooled) air driven by the blower or fan 60 will flow through the duct chamber 52, and provide an even air flow over the body of the patient. The outlet openings 56 are provided with deflector vane covers if desired. The housing cover 36 can be counter balanced with a pneumatic cylinder if desired, as well.

Electric vibrators shown at 66A and 66B are mounted onto the bed 14. The bed 14 is supported on the suitable elastomeric members 15 to walls of the base so that the bed 14 will vibrate when the electric vibrators 66A and 66B are energized. The vibrators 66A and 66B are placed at desired locations for obtaining a therapeutic or pleasurable vibration during use. The vibration intensity and frequency can be changed with suitable controls, as desired.

The vibrators are divided into two groups, one of which is below the legs and knees of the user, and used vibrators 66A. Several vibrators can be placed in this general region, and they are independently controlled as a group. Controls for the vibrators may be on the control panel accessible to the user, but preferably are on one of the side wings 18, on the exterior as shown so that an attendant can control the vibration of frequency, intensity, and the location of the vibration. The vibrators 66B are in a section underneath the back and the shoulders of a patient. These vibrators can be varied in size and location, and then varied in intensity to obtain selective vibration for example, in two different locations, namely the legs (66A), as well as under the back, and then varied in intensity as well. Both groups of vibrators can be operated simultaneously for total body vibration.

Figure 3:
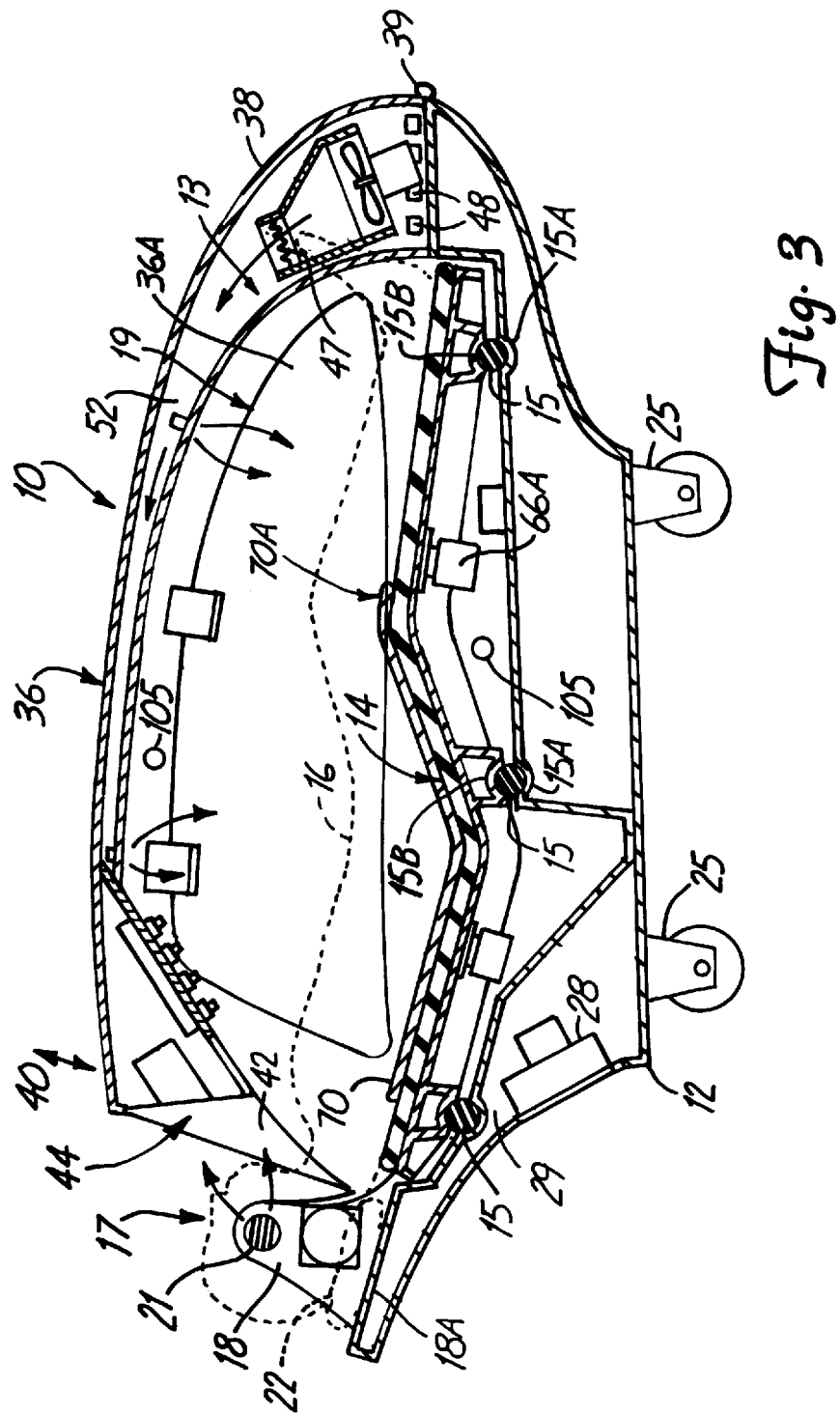
FIG. 3 is a longitudinal sectional view thereof showing the interior construction.

In certain instances, it is desirable to have extra heat added in particular locations of the body, and as can be seen in FIGS. 1 and 3 a supplementary conventional heating pad or blanket indicated at 70 can be placed over the top of the bed 14, particularly as shown from a region below the shoulders up to under the knees which is indicated at 70A. This entire pad can be heated with suitable controls that are schematically shown, and the temperature can be adjusted.

Controls can be made for the attendant, and as shown may be located on the exterior of the housing, for example up near one of the wings 18 shown in FIG. 1, can include a temperature control indicated at 70B for the extra heating blanket, as well as controls indicated at 72 for controlling the individual vibrator 66A and 66B. These controls 72 can be adjustable controls to control the intensity of vibration, in the individual sections of the bed. In other words, the person can have vibration applied to the lower portions of the body, generally below the waist, or to the upper portions of the body, or to both. Further, a thermostat control 73 can be set to adjust the heat in the interior atmosphere of the body compartment of the capsule which surrounds the patient.

A program can be established for controlling the atmosphere temperature in a desired cycle, or at set levels. For example, a pre-programmed set of temperatures can include a basal body temperature of 100° F. or 38° C., a low heat setting that would be higher than the basal body temperature and in the range of 120° F. or 49° C.; a low to moderate heat setting of between 100° F. and 145° F. which is 49° C. to 63° C. Moderate heat would be the higher settings shown.

A moderate to high heat scale would be from 145° F. up to 175° F., which would usually be the maximum. This is 63° C. to 79° C. the 175° F. temperature is as hot as the system normally would be operating.

The casters 25 shown are locking casters, 60 that the capsule can be set and in place and it will stay there, but the casters can be released for movement.

Figure 6:
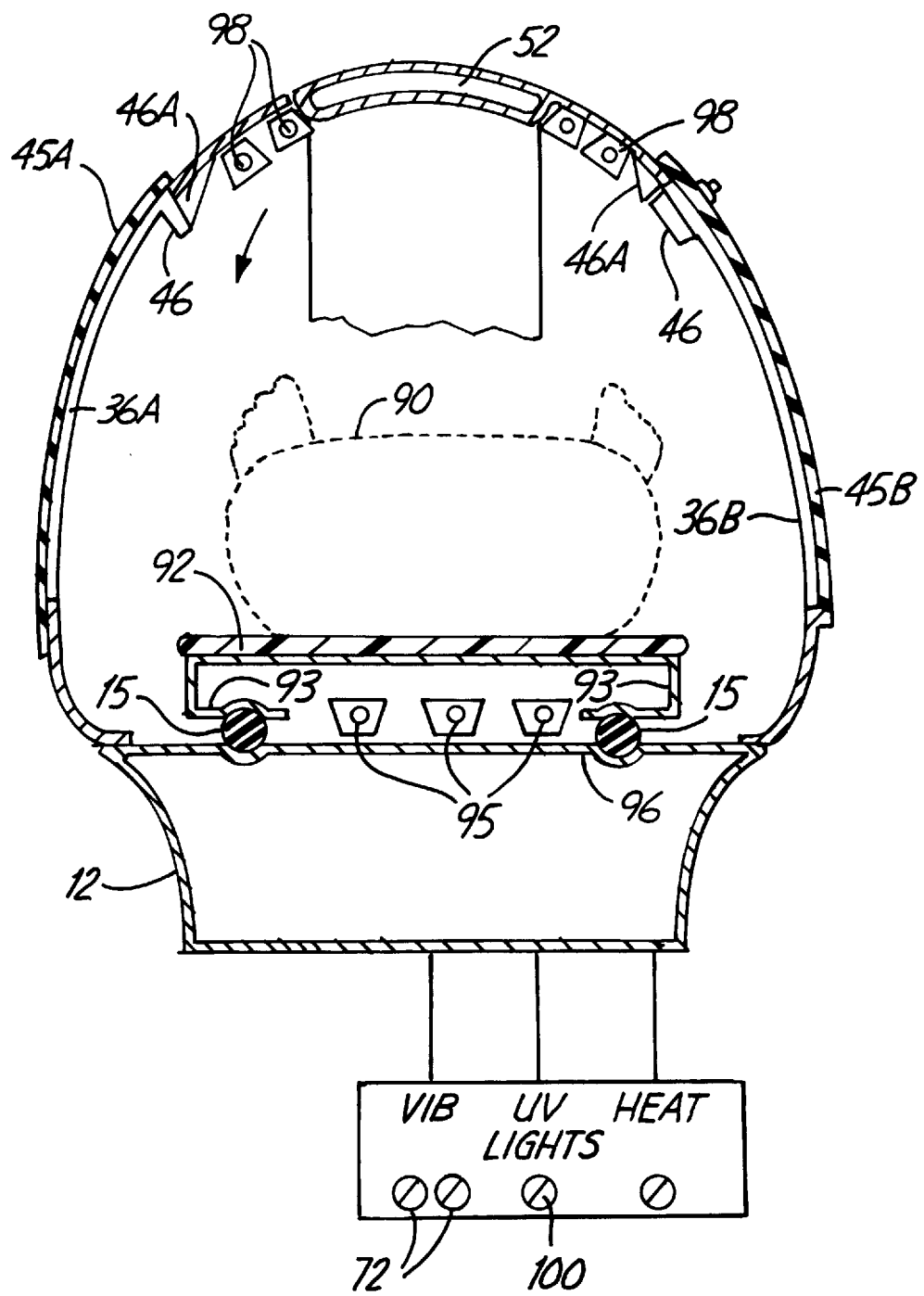
FIG. 6 is an enlarged sectional view similar to FIG. 4 showing a modified form of the invention including UV light application.

In addition to the heat therapy, that is available, FIG. 6 illustrates a modified form of the invention in which ultra violet light can be applied to the body of the patient, to treat skin rashes or psoriases with ultra violet light and other known light techniques.

In this form of the invention, the capsule, the openings, and the window covers are all the same as before, as is the pedestal arrangement and the duct arrangement for carrying heated air to a patient illustrated in dotted lines 90.

In this form of the invention, however, the full contour bed has been replaced with an acrylic platform bed 92 which has suitable supports 93 that rest on the elastomeric material balls 15 so that the unit is vibration isolated, for ease of interchanging the two types of beds. vibrators could be added to the acrylic bed 92, if desired. The acrylic bed 92 is clear, so light will transmit through it, and as shown an array of ultra violet lights 95 are mounted on a floor 96 of the pedestal, and are used with suitable reflectors to reflect light upwardly onto the body 90 of the patient. Additionally, ultra violet lights shown at 98 are provided in the cover and extend along the length of the cover. They are shown as a cross section in FIG. 6, but would be elongated and extend along the length of the cover so that the ultra violet light would radiate down onto the top of the patient.

Ultra violet light radiation has been used for treating of psoriases, and other skin afflictions, and the amount of ultra violet can be controlled by controlling the number of lights that are turned on, as well as the intensity of the lights utilizing a suitable control 100 shown also in FIG. 6. FIG. 6 shows vibrator controls and heat controls as well in a remote control panel.

It should be noted that if light therapy is going to be used for treating skin disorders, no sheets or padding would be placed on the acrylic bed 92, but it can be contoured to be as comfortable as possible for a patient lying on the clear acrylic platform or bed.

The windows 36A and 36B are again accessible for opening or closing to gain access to the patient to adjust the patient if desired and to check on other conditions. The patient can be observed through these windows, so that the patient does not have to be disturbed for mere observation, as is necessary for when a solid cover is utilized and has to be opened.

The heat coming from above assures the patient that the patient is warm even when utilizing the light therapy shown in FIG. 6. The temperature can be maintained by having one or more temperature sensors 105 in the capsule which are connected to the thermostatic heater controls warm to a suitable temperature as set by the controls.

For spinal cord injury patients the unit helps alleviate pressure sores because of its vibration and conformability, particularly when used with a suitable pad, and will temporarily increase grutaneous blood flow and well as decrease muscle spasms. Patients in chronic pain will receive temporary relief from aches and pains, and the audio therapy aids in directing ones attention away from such pain.

For stress management therapy, the unit will aid in relaxing the muscles, calm the mind, and again audio therapy can be used. The temporary increase in circulation is helpful for diabetic patients as well as general vascular surgery and post-operative patients, for regular surgery and orthopedic surgery. Persons with physiatric or physiological problems are calmed, muscle relaxation occurs, and this can reduce the need for anti-depressants.

Persons with sciatica also are able to get some relief because of the improvement in circulation caused by the raised temperature and the temporary relief of aches and pains caused by the vibration as well as the raised temperatures.

Although the present invention has been described with reference to preferred embodiments, workers skilled in the art will recognize that changes may be made in form and detail without departing from the spirit and scope of the invention.

What is claimed is:

1. A physical therapy personal treatment device having a support pedestal and an elongated generally horizontally extending bed supported by the pedestal, the pedestal having longitudinal side edges, and forming a head rest at a first end, a person using the treatment device lying on the bed with a head on the headrest, comprising:

a cover member above the bed having sides with side edges aligning with the side edges of the pedestal and extending substantially along longitudinal sides of the bed to overly the bed and enclose a space for a person on the bed, the cover terminating at a head end to leave only the head rest uncovered; and the cover member being hinged to the bed adjacent an end opposite the headrest, and openable to cause a head end to move away from the bed sufficiently to permit a person to enter and leave the bed, the cover member having a window opening along at least one of the sides of the cover member, said window opening extending for a substantial portion of a longitudinal length of said cover member along the at least one side, to provide for an opening leading into the space occupied by a person lying on the bed;

a heater providing heat outlets in the cover member only to direct heat downwardly onto a body of a person lying on the bed with heat outlets only within the space enclosed by the cover member;

a plurality of ultraviolet lights mounted on the cover member and being solely within the space enclosed by the cover member when the cover member is closed thereby directing light downwardly toward the bed, the cover having a wall providing a neck opening so when the cover member is closed the head of the person lying on the bed with the head on the headrest is to the exterior of the cover member; and a window member for covering the window opening, said window member being of a transparent material, and hingedly attached to the cover member and movable between an open and a closed position, thereby being carried by the cover.

2. The device of claim 1 including a pair of hinges for hinging the window member relative to the cover along an upper edge thereof, said window member having a lower edge that is liftable to extend outwardly from the cover member and to move to a level above the hinge members in the window member open position.

3. The device of claim 1, wherein said bed comprises a transparent sheet of material for supporting a patient, and a light source below the transparent bed for directing light upwardly onto a person lying on the top of the bed, said light source being completely within the space defined by the pedestal and cover member.

4. The device of claim 1 and lockable casters for supporting the pedestal relative to a support surface.

5. The device of claim 1 wherein there are two window openings, one on each side of the cover member, and operable window members for covering the window openings.

6. The device of claim 1, and a plurality of vibrators mounted to vibrate the bed, the vibrators being operable in separated groups, one group on each of a plurality of different bed sections.

7. The device of claim 6, and a separate heater, which is separately controllable as to temperature placed on the bed.

8. The device of claim 6, wherein said vibrators are divided into two separated groups, a first group being positioned in a region of the bed that is underneath legs and knees of the person lying on the bed, and the other group of vibrators being mounted to vibrate the bed in a region underneath a back and shoulders of a person on the bed.

9. The device of claim 6, wherein said headrest region comprises a headrest having a pair of upwardly extending wings, said wings extending along the sides of a head of a user of the device, and controls for controlling the light, heat and vibration on the exterior of the wing accessible to an operator on the exterior of the device.

* * * * *